US008663099B2

(12) United States Patent
Tydlaska et al.

(10) Patent No.: US 8,663,099 B2
(45) Date of Patent: Mar. 4, 2014

(54) SYSTEM AND METHOD OF INSERTION INTO AN OROPHARYNGEAL AREA

(76) Inventors: Jay (Jason) Tydlaska, Fort Worth, TX (US); Amy Sheppard, Fort Worth, TX (US)

(*) Notice: Subject to any disclaimer, the term of this patent is extended or adjusted under 35 U.S.C. 154(b) by 13 days.

(21) Appl. No.: 13/373,880

(22) Filed: Dec. 5, 2011

(65) Prior Publication Data
US 2012/0178997 A1 Jul. 12, 2012

Related U.S. Application Data

(62) Division of application No. 12/750,784, filed on Mar. 31, 2010.

(60) Provisional application No. 61/165,091, filed on Mar. 31, 2009, provisional application No. 61/422,600, filed on Dec. 13, 2010.

(51) Int. Cl.
A61B 1/267 (2006.01)

(52) U.S. Cl.
USPC .............. 600/186; 600/194; 600/185

(58) Field of Classification Search
USPC ................................ 600/185–199
See application file for complete search history.

(56) References Cited

U.S. PATENT DOCUMENTS

| 2,646,036 | A |   | 7/1953  | Allyn et al. |
|-----------|---|---|---------|--------------|
| 4,185,639 | A |   | 1/1980  | Linder |
| 4,832,020 | A | * | 5/1989  | Augustine ............ 128/207.14 |
| 4,834,077 | A |   | 5/1989  | Sun |
| 4,979,499 | A |   | 12/1990 | Sun |
| 5,487,607 | A |   | 1/1996  | Makita et al. |
| 5,645,519 | A | * | 7/1997  | Lee et al. ................. 600/114 |
| 5,743,849 | A |   | 4/1998  | Rice et al. |
| 5,766,202 | A |   | 6/1998  | Jones et al. |
| 5,800,344 | A |   | 9/1998  | Wood, Sr. et al. |
| 5,810,770 | A |   | 9/1998  | Chin et al. |
| 5,846,186 | A |   | 12/1998 | Upsher |
| 6,142,144 | A |   | 11/2000 | Pacey |
| 6,146,402 | A |   | 11/2000 | Munoz |
| 6,248,061 | B1|   | 6/2001  | Cook, Jr. |
| 6,354,993 | B1|   | 3/2002  | Kaplan |
| 6,494,826 | B1|   | 12/2002 | Chatenever |
| 6,543,447 | B2|   | 4/2003  | Pacey |

(Continued)

FOREIGN PATENT DOCUMENTS

WO          9855170      12/1998
WO          02051304      7/2002

(Continued)

Primary Examiner — Kevin T Truong
Assistant Examiner — Christian Sevilla
(74) Attorney, Agent, or Firm — Decker Jones et al.; Brian K. Yost; Geoffrey A. Mantooth

(57) ABSTRACT

In accordance with the present design there is provided a method utilizing a novel laryngoscope design that inserts a bougie along a canal on one side of a sheath; the sheath being further comprised of a canal capable of being threaded with a bougie, providing a method of access for guiding a Bougie into the trachea, while facilitating a method for the removal of oral/pharyngeal secretions, by placing a suction catheter in a canal through which a method for creating suction is provided; and further the bougie canal provides a method of facilitating placement of a topical anesthetic by providing a channel through which a local anesthetic can be sprayed.

11 Claims, 14 Drawing Sheets

(56) References Cited

U.S. PATENT DOCUMENTS

| | | |
|---|---|---|
| 6,569,089 B1 | 5/2003 | Covington et al. |
| 6,655,377 B2 | 12/2003 | Pacey |
| 6,666,819 B2 | 12/2003 | Heine |
| 6,817,973 B2 | 11/2004 | Merril et al. |
| 6,840,903 B2 | 1/2005 | Mazzei |
| 6,843,769 B1 | 1/2005 | Gandarias |
| 6,890,298 B2 | 5/2005 | Berci et al. |
| 7,044,909 B2 | 5/2006 | Berci et al. |
| D534,652 S | 1/2007 | McGrath |
| 7,347,863 B2 | 3/2008 | Rothe et al. |
| D590,501 S | 4/2009 | McGrath |
| 7,695,433 B2 | 4/2010 | Simons |
| 8,187,180 B2 * | 5/2012 | Pacey .......................... 600/245 |
| 2001/0014768 A1 | 8/2001 | Kaplan |
| 2002/0082478 A1 | 6/2002 | McGrath |
| 2004/0127770 A1 | 7/2004 | McGrath |
| 2006/0020166 A1 | 1/2006 | Berall |
| 2006/0165152 A1 | 7/2006 | Walker et al. |
| 2006/0276693 A1 | 12/2006 | Pacey |
| 2006/0276694 A1 * | 12/2006 | Acha Gandarias ........... 600/194 |
| 2007/0179342 A1 | 8/2007 | Miller et al. |
| 2007/0197873 A1 | 8/2007 | Birnkrant |
| 2007/0299313 A1 | 12/2007 | McGrath |
| 2008/0045801 A1 | 2/2008 | Shalman et al. |
| 2008/0177146 A1 | 7/2008 | Chen |
| 2008/0177147 A1 | 7/2008 | Simons |
| 2008/0249370 A1 | 10/2008 | Birnkrant et al. |
| 2009/0299146 A1 | 12/2009 | McGrath |

FOREIGN PATENT DOCUMENTS

| | | | |
|---|---|---|---|
| WO | 2004/096032 | 11/2004 | |
| WO | 2004096031 | 11/2004 | |
| WO | 2004096032 | 11/2004 | |
| WO | 2008138119 | 11/2008 | |
| WO | WO 2008138119 A1 * | 11/2008 | ............ A61M 16/04 |
| WO | 2010100497 | 9/2010 | |

* cited by examiner

SYSTEM AND METHOD OF INSERTION INTO AN OROPHARYNGEAL AREA

CROSS REFERENCE TO RELATED APPLICATIONS

This application is a divisional which claims the benefit of US Published Application US 2010/0249513 A1 filed on Mar. 31, 2010, which claims the benefit of PPA No. 61/165,091, filed on Mar. 31, 2009 referenced by incorporation herein which claims the benefit of PPA 61/422,600 filed Dec. 13, 2010 by the present inventor.

BACKGROUND OF THE PRESENT DISCLOSURE

Over 20 million intubation procedures are performed each year in the United States either as a routine part of surgery or in emergency situations resulting from trauma, cardiopulmonary arrest or other disease processes. In an intubation procedure, it is necessary to insert an endotracheal tube (ET tube) in order to maintain a patient's respiratory function. The tube is inserted into a patient's trachea via either the mouth or nasal tract so that the airway remains open and oxygen reaches the patient's lungs.

Practitioners use an instrument known as a laryngoscope to help in the placement of endotracheal tubes. The practitioner uses the device to move the tongue and epiglottis to one side so that the airway may be properly identified. In a small percentage of patients, the airway cannot be identified with the laryngoscope alone. With these patients, practitioners sometimes use a device known as a "bougie". This bougie is a small diameter flexible cylinder of metal, plastic or other material that may serve as a guide for placement of a larger ET tube.

When performed by an experienced practitioner, the procedure is usually quick and uneventful. Even in the hands of well skilled individuals, there is an unacceptable number of occurrences in which placement of the endotracheal tube is difficult or impossible resulting in an inability to provide the patient with oxygen leading to death or injury. Difficulty in placing the endotracheal tube may be due to trauma, abnormal anatomy, disease processes or for unknown and unpredictable reasons.

Over the years, there have been many attempts to improve upon the design of the original laryngoscope, but those attempts have been largely unsuccessful as evidenced by the continued use today of virtually the same device developed in the 1940's.

More recently due to advances in miniaturization of technology, devices have been developed known as video laryngoscopes that greatly improve the ability to adequately locate the vocal cords and appropriately place the endotracheal tube. These devices are generally constructed with a small camera placed at the distal end of the laryngoscope and the image obtained by that camera is viewed on a remote monitor. These devices are expensive and often inconvenient to use. Prior art devices fail to offer a solution to the difficult intubations in which a bougie is necessary. What is needed is an inexpensive, sanitary, easy to use laryngoscope system that may be used in all situations, including the most difficult intubations in the most challenging environments to provide better access would be advantageous to provide an aspect of the present disclosure, where the arm is removably coupled to the handle.

In another aspect of the present disclosure, a user using the ejection element ejects the sheath without touching the sheath.

In another aspect it would be advantageous that the canal's curvature provides tension against the bougie and other flexible tubing preventing such tubing from slipping against the canal.

Further the sheath, it would be advantageous to remotely eject by depressing a thumb ejector switch on the handle releasing a clasp at the coupling point, further releasing a spring element held in compression which, releasably, forcibly moves the sheath along the length of the arm, such that the sheath becomes detached from the arm.

SUMMARY OF THE PRESENT DISCLOSURE

In accordance with the present design there is provided an inexpensive, sanitary, easy method utilizing a novel laryngoscope design that when used in all situations, including most difficult intubations in challenging environments, provides for multiple tube insertions through the use of a method of inserting a bougie or other endotracheal tubes utilizing a canal along the one side of a sheath.

The present disclosure generally provides a laryngoscope capable of being connected to a monitor and power source, said laryngoscope being comprised of a handle, an arm and a disposable sheath; wherein the sheath is slide ably and removably coupled to the arm; the sheath being further comprised of a canal capable of being threaded with a bougie; the handle being further comprised of a remote ejection element mechanically connected to a spring element capable of ejecting the sheath from the arm; the arm being removably coupled to the handle. The sheath is further comprised of a small "C"-shaped canal at least partially running along the outside length that serves as a guide for the bougie. The sheath channel and guide for the bougie further provides for a method of access for multiple tubes through a method of guiding an endotracheal tube into the trachea, while facilitating a method for the removal of oral/pharyngeal secretions by providing a channel through which a method for creating suction, utilizing a suction catheter is placed; and the bougie canal provides a method of facilitating placement of a topical anesthetic by providing a channel through which a local anesthetic can be sprayed. With the laryngoscope placed, the practitioner threads a bougie through the sheath's channel of the bougie into the airway and uses this bougie as a guide for the ET tube.

The sheath may be remotely ejected by depressing a thumb ejector switch on the handle releasing a clasp at the coupling point and releasing a spring element held in compression which, upon release, forcibly moves the sheath along the length of the arm, detaching the sheath from the arm.

DESCRIPTION OF AT LEAST ONE EMBODIMENT

Figure 1:
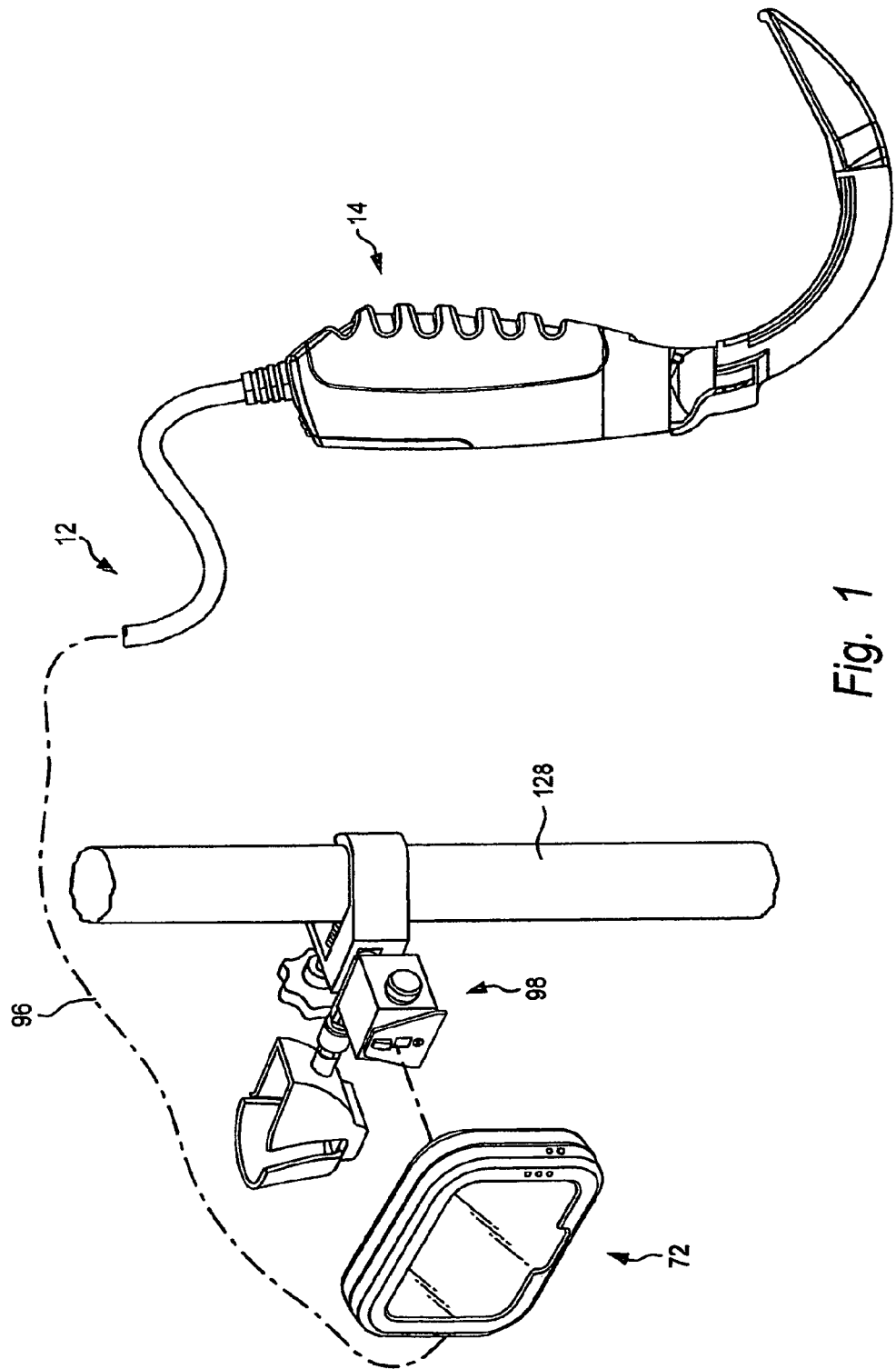
FIG. 1 is a side perspective view of the laryngoscope system in accordance with a preferred embodiment.

Referring to FIGS. 1-15 there is shown a laryngoscope system 12 of the present invention. This laryngoscope system 12 is generally comprised of a laryngoscope 14, a display unit 72, and an IV pole attachment 98 capable of being coupled to an IV pole 128.

Figure 2A:
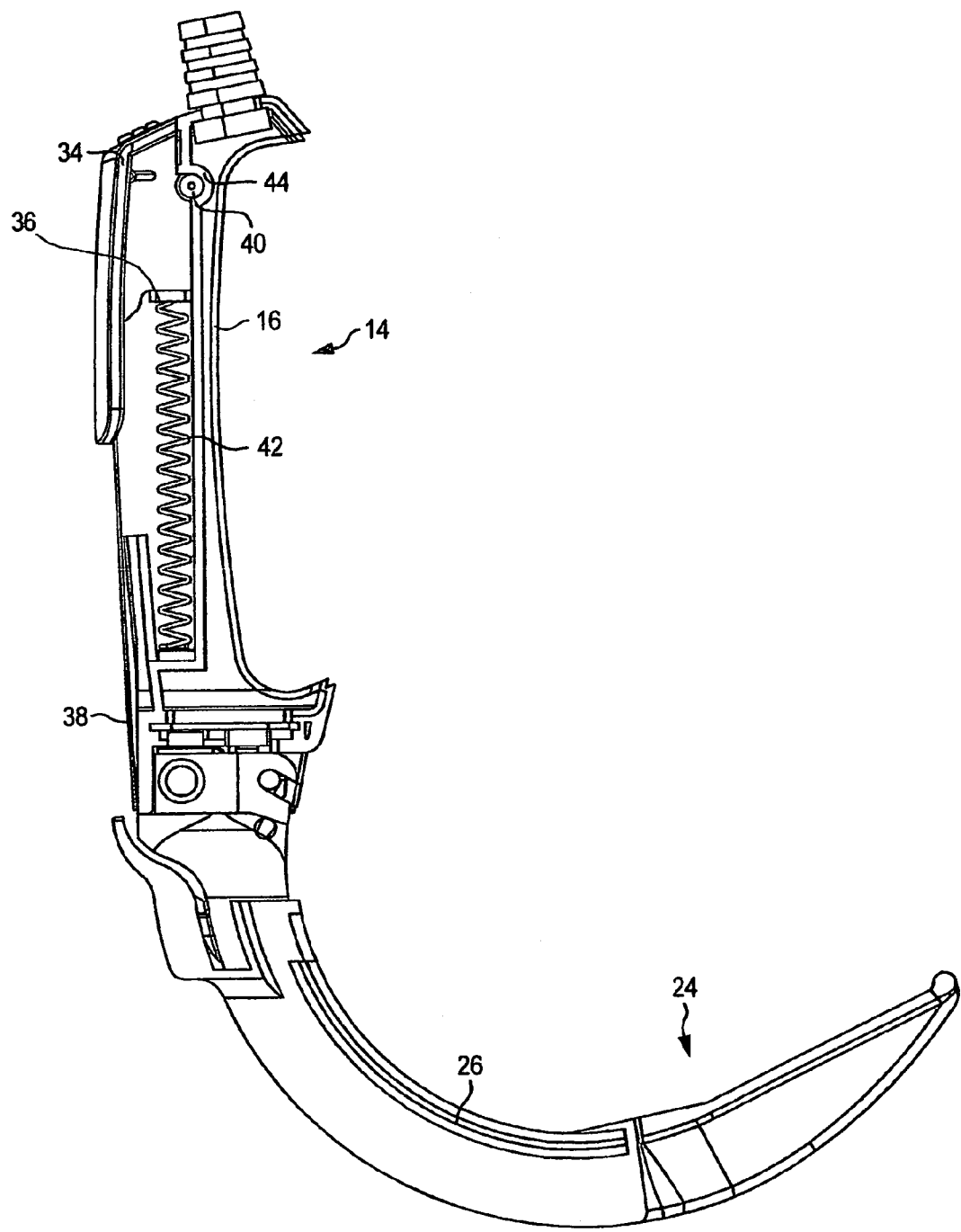
FIG. 2A is an isometric cut-away right side view of the laryngoscope in the open position with the arm 14 and sheath 10 attached in accordance with a preferred embodiment.
Figure 2B:
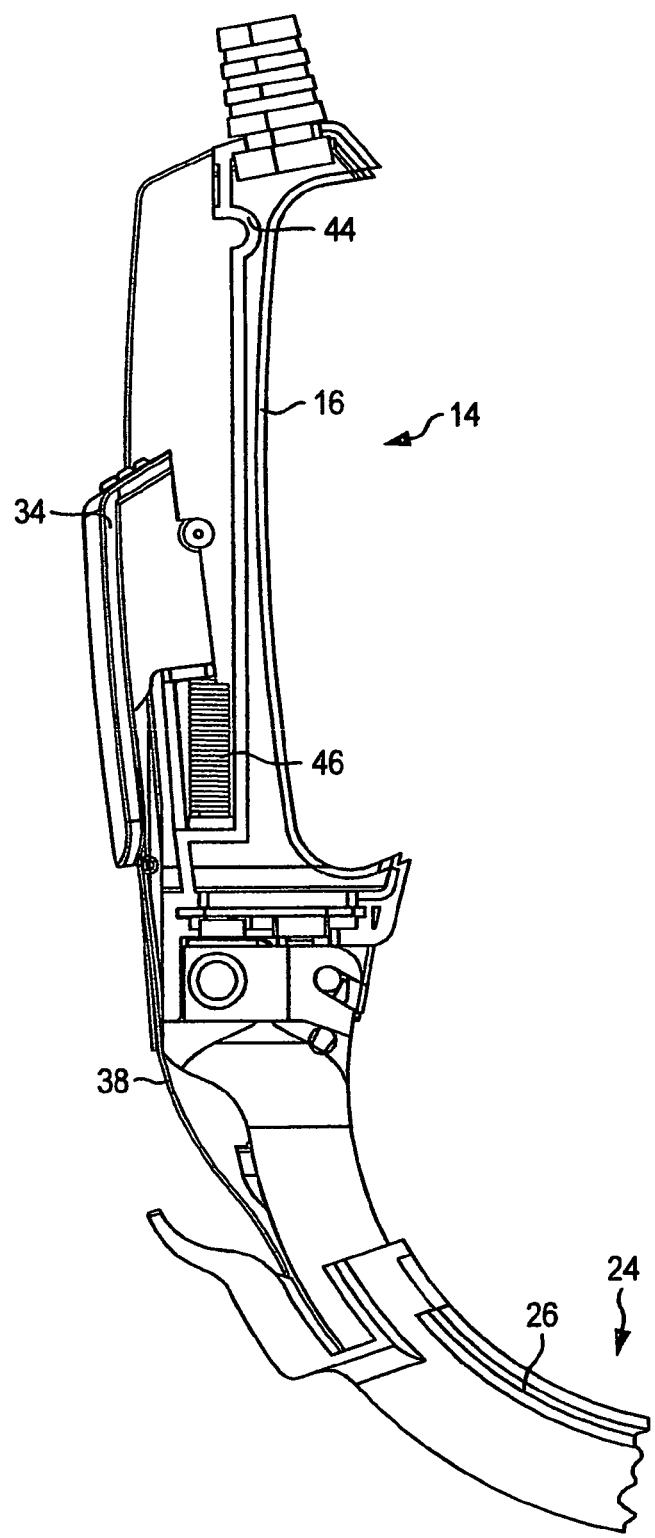
FIG. 2B is an isometric cut-away right side view of the laryngoscope of FIG. 2A with the thumb ejector 20 switch in the extended position.
Figure 3:
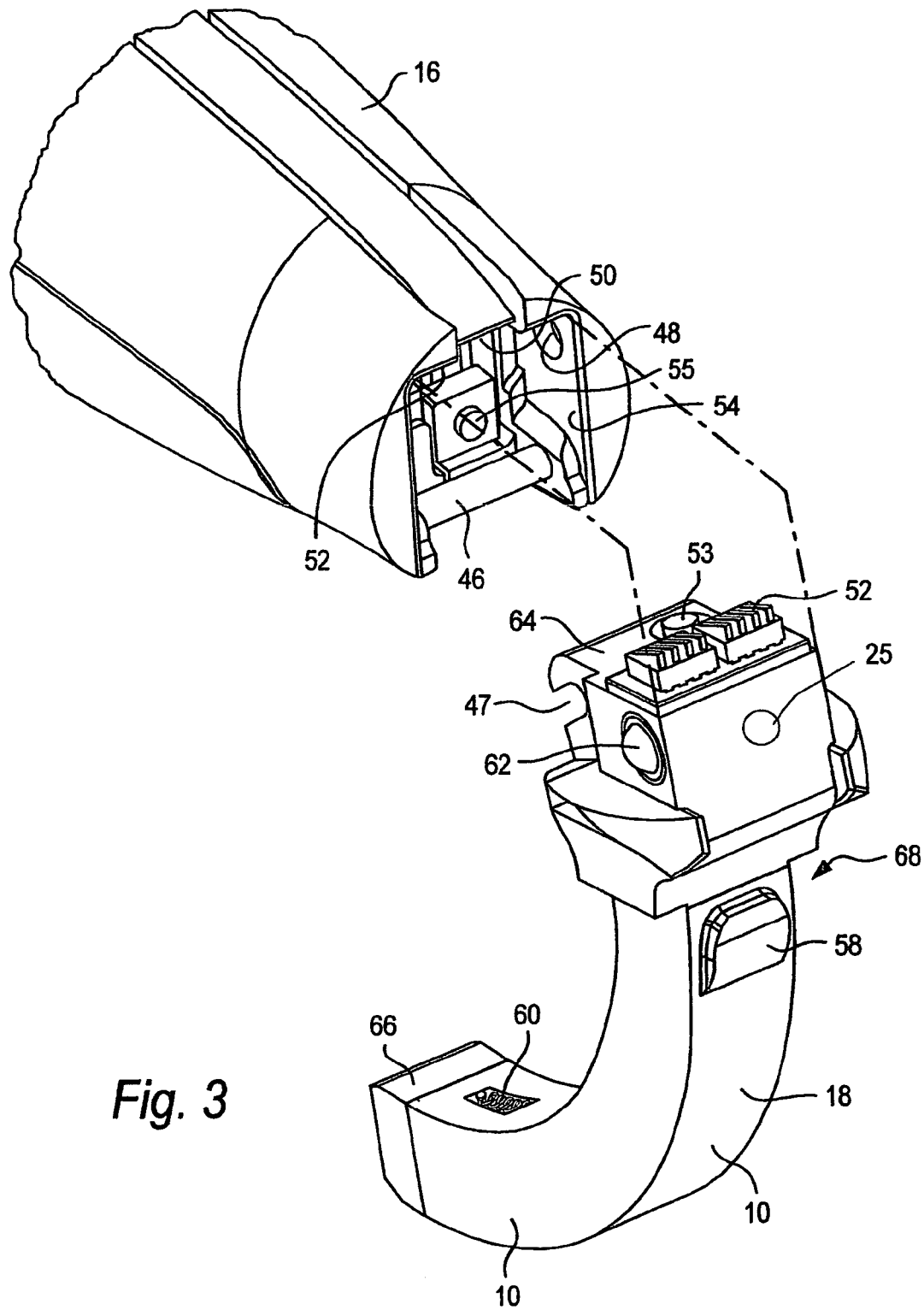
FIG. 3 is an isometric, rear, and side view of the laryngoscope arm 14 and a partial view of the laryngoscope handle, in accordance with a preferred embodiment.
Figure 4:
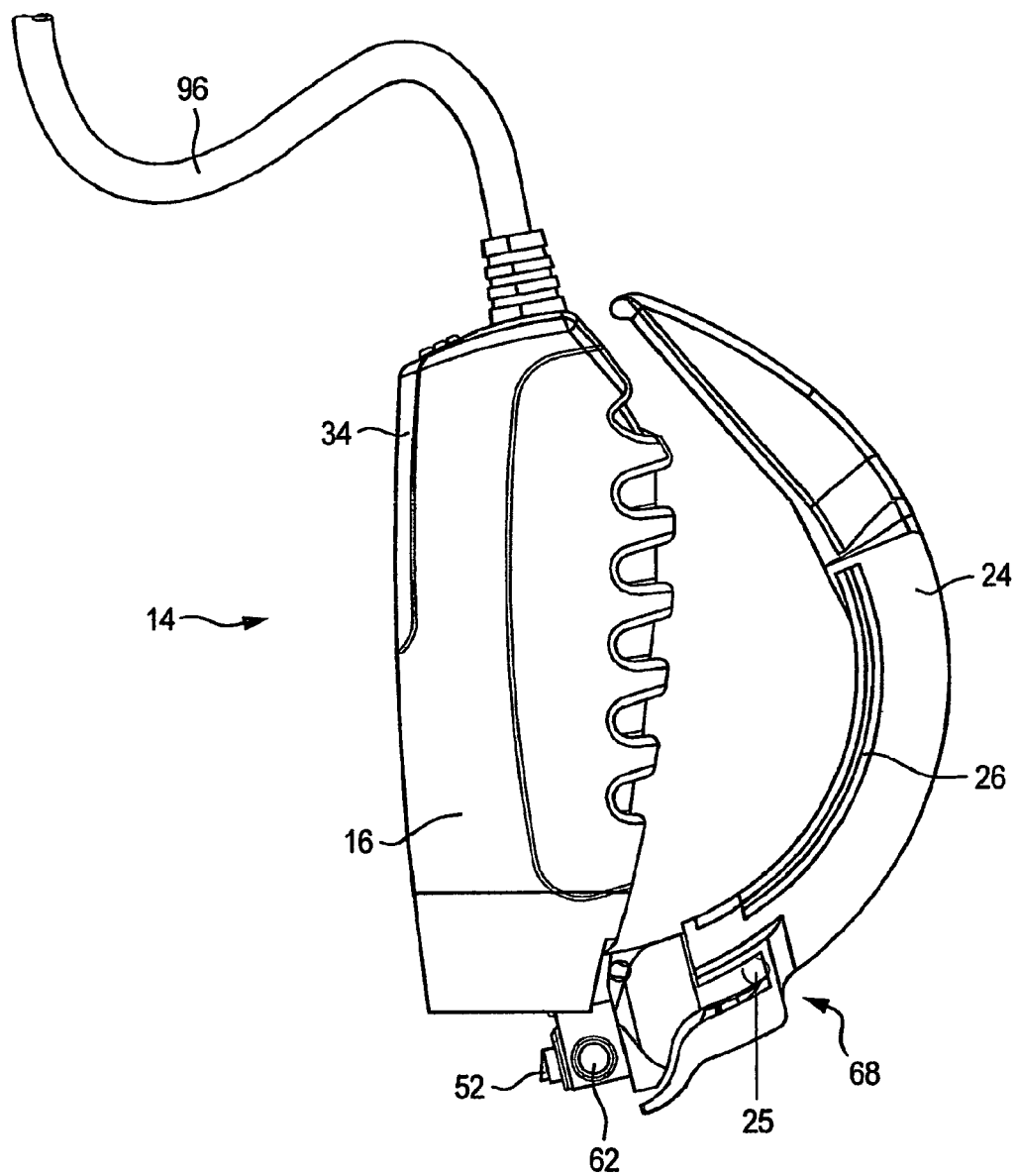
FIG. 4 is an isometric right side view of the laryngoscope with the arm 14 in the closed position in accordance with a preferred embodiment.
Figure 5:
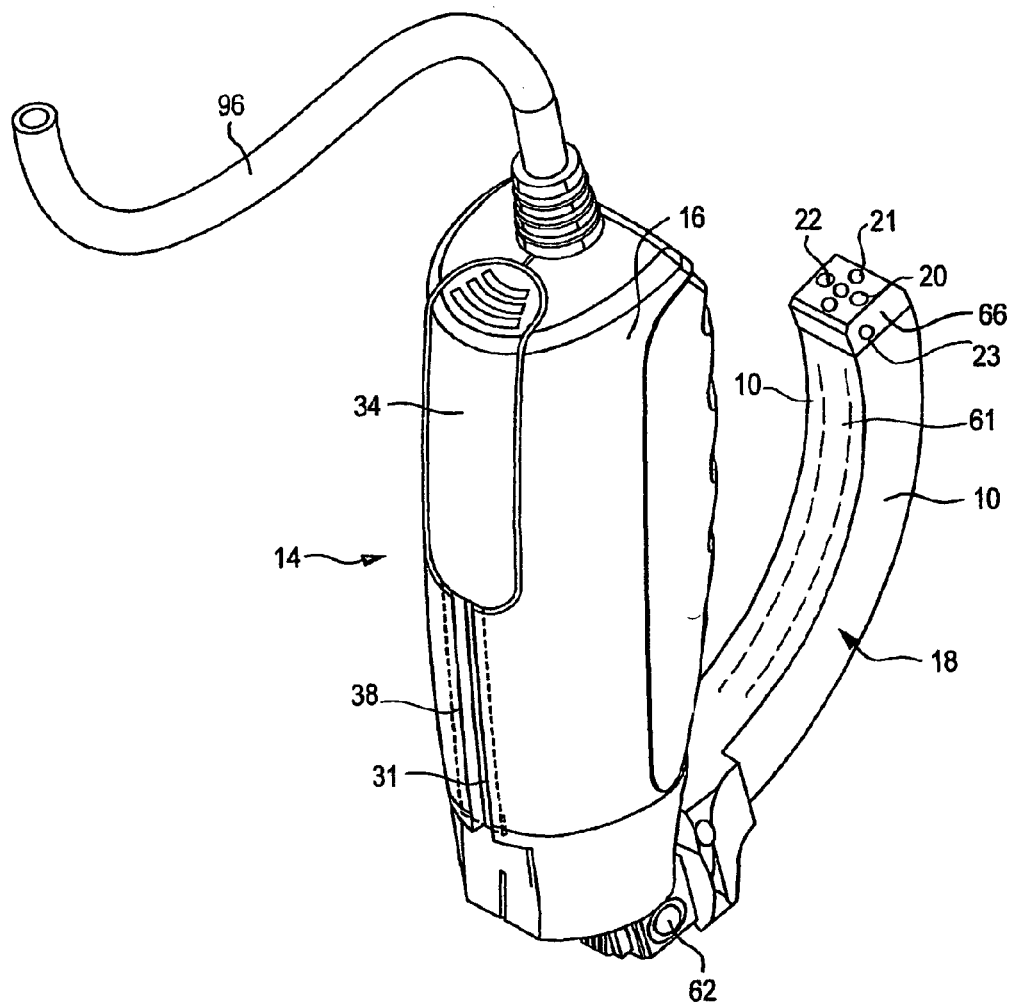
FIG. 5 is an isometric right side and rear view of the laryngoscope with the arm 14 in the closed position without the sheath 10 attached in accordance with a preferred embodiment.
Figure 6:
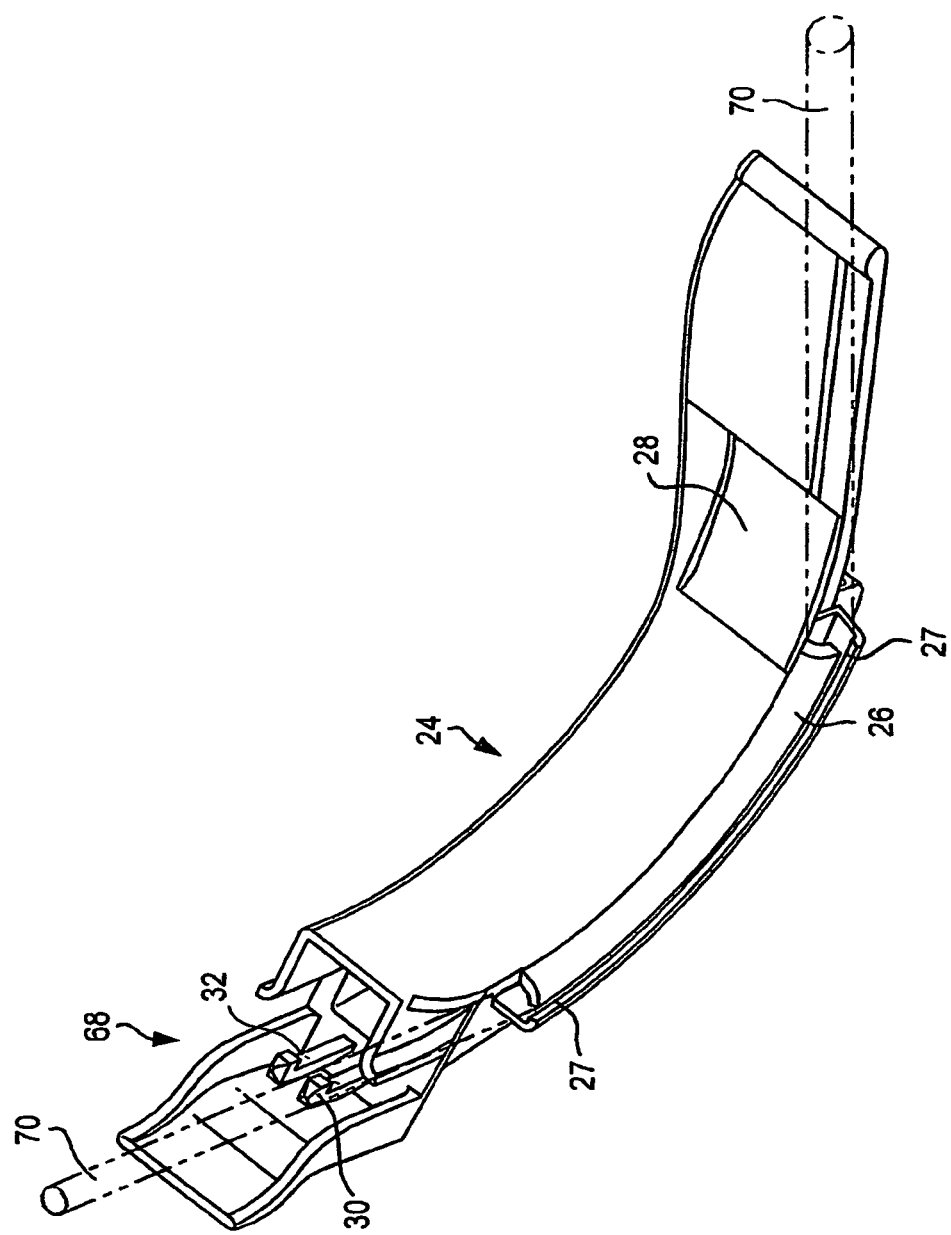
FIG. 6 is an isometric right side, top view of the sheath 10, in accordance with a preferred embodiment.

Referring to FIGS. 1-6, the laryngoscope 14 of the present invention comprises a handle 16, a curved blade or arm 14 18, a light 20, a camera 16 22, and a disposable sheath 10 24. The handle 16 of the laryngoscope 14 has a curved arm 14 18 attached. In one aspect of the present invention, the arm 14 18 is removably coupled to the handle 16. Slideably coupled to the arm 14 18 is a sheath 10 24 which snaps into place at a coupling point 68 (FIG. 3). In the preferred embodiment this sheath 10 24 is formed from plastic and is at least partially clear so as to allow light emitted from the light 20 to pass through it. Referring to FIG. 6, in the preferred embodiment, the sheath 10 24 is comprised of a transparent window 28. The sheath 10 24 has one or more clasps 30 on its proximal end (FIG. 6) which may be removably coupled to the arm 14 18 at the coupling point 68 (FIG. 3). In one aspect of the present invention, a user, using the thumb ejector 20 switch 34, may eject the sheath 10 24 without physically touching the sheath 10 24. Referring to FIGS. 2A, 2B and FIG. 5, the thumb ejector 20 switch 34 is located at the upper end of the handle 16. The thumb ejector 20 switch 34 is comprised of a plunger block 36, an ejection rod 38, and a protrusion 40. The thumb ejector 20 switch 34 is coupled to the ejection rod 38 which is coupled at the top end with the plunger block 36. The plunger block 36 is comprised of the protrusion 40. A return spring 42 is coupled to the thumb ejector 20 switch 34. This return spring 42 maintains the ejection rod 38 in a retracted position as a rest state (FIG. 2A). Above the plunger block 36 is a retaining receptacle 44. This retaining receptacle 44 is structured and arranged such that it is capable of nesting the protrusion 40 and maintains the thumb ejector 20 switch 34 in a rest position and prevents accidental deployment of the ejection rod 38.

Referring to FIGS. 2B, 3, 5 and 6, the sheath 10 24 may be remotely ejected by depressing the thumb ejector 20 switch 34 (FIG. 2B) on the handle 16 which releases the clasp 30 at a sheath 10 connection ridge 58 located on the arm 14 18 at the coupling point 68. The thumb injector switch 34, when depressed, travels down a switch channel 31 (FIG. 5). In one embodiment, thumb ejector 20 switch 34 further releases a spring element 60 (FIG. 3) held in compression which, upon release, forcibly moves the sheath 10 24 along the length of the arm 14, such that the sheath 10 becomes detached from the arm 14. Referring to FIG. 6, in one aspect of a preferred embodiment, the clasp 30 has a score line 32 or thinner layer of material. This score line 32 creates a weakened area in the clasp 30 so that when depressed by the ejection rod 38, the clasp 30 is deformed at the score line 32. In one aspect of the present invention, the clasp 30, after ejection, cannot be returned to its original un-deformed configuration without breaking at the score line 32. Such breaking prevents the sheath 10 from being reused and thus, helps prevent contamination.

In one embodiment of the invention, and as shown in FIG. 6, the sheath 10 is further comprised of a small canal 12 running at least partially along the outside length that serves as a guide for a bougie 70. With the laryngoscope 14 properly placed, the practitioner may thread the bougie 70 through the sheath's bougie canal 12 into the airway and use this bougie 70 as a guide for an ET tube (not shown). As shown in the FIG. 6, in the preferred embodiment, this canal 12 is open on one side 27 such that the bougie 70 may be inserted and removed through this open side 27. This open side 27 permits the user to maintain the laryngoscope 14 in the airway while threading the ET tube over the bougie 70. In this embodiment, the bougie 70 is forced out of the canal 12 through the side opening 27 by the ET tube. In the preferred embodiment, this canal 12 with its open side 27 is "C" shaped. This "C" shape helps maintain the bougie 70 within the canal 12 while still allowing the bougie 70 to be removed through the open side 27. Although the canal 12 of the preferred embodiment is open and forms a "C" shape, the canal 12 need not be open and need not be "C" shaped. Rather, the canal 12 can be closed on the sides so as to completely surround the bougie 70 along its length and can be circular or any other suitable shape.

As best shown in FIG. 5, the laryngoscope 14 also has a light 20 and a camera 16 positioned at the distal end of arm 14 and confined within arm 14 walls 10 beneath a transparent cap 66. This cap 66 is clear and allows light to reach the lens 56 and light generated from the light 20 to exit the arm 14. A lens 56 for this camera 16 is located in the arm 14 18 and the signal is transmitted through a cord 96 to a display unit 72. While in the preferred embodiment the camera 16 is solid state and does not rely upon mirrors or prisms, the camera 16 may be comprised of a lens 56 that focuses light as an image on a prism. The image may then reflected by the prism to the camera 16 22.

Figure 12:
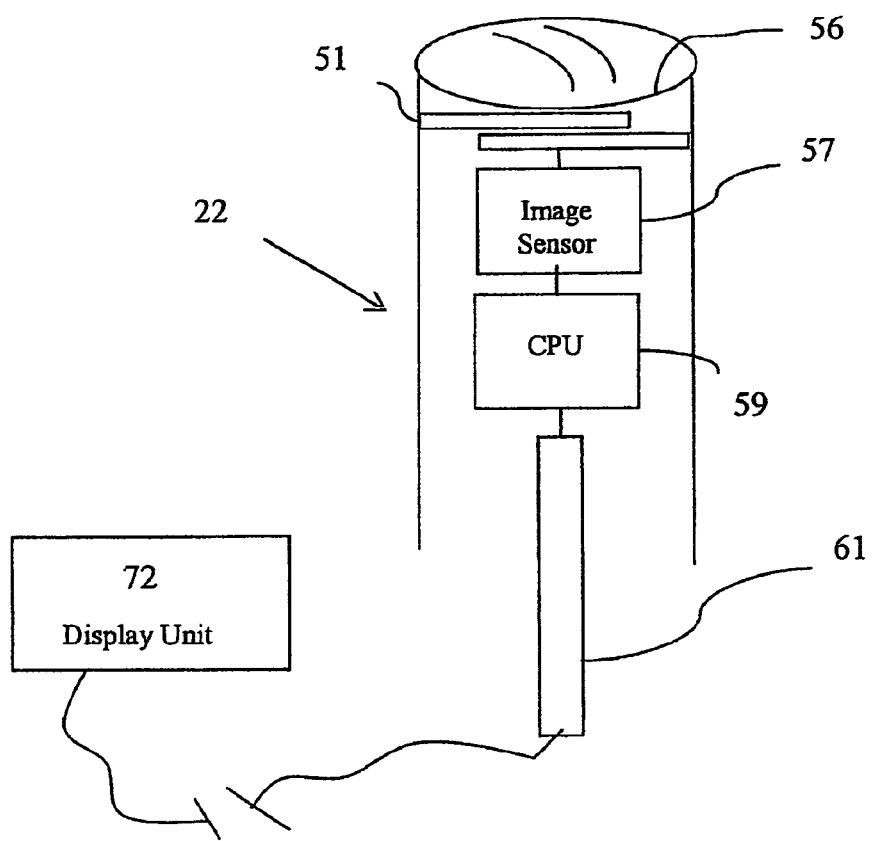
FIG. 12 is a block diagram depicting the camera 16 unit.

Referring to FIGS. 5 & 12, the lens 56 of the camera 16 is also located at the distal end of the arm 14. In another embodiment, the main portion of the camera 16 is located in the handle 16 and communicates with the lens 56 through a fiber optic cable. In one embodiment, the camera 16 transmits the signal directly to the display unit 72 without the use of mirrors and prisms. In the preferred embodiment, the camera 16 is a complementary metal-oxide-semiconductor (CMOS) camera 16. However, other cameras 22 may be used including those incorporating charge-coupled device (CCD) technology.

In the preferred embodiment, the camera 16 transmits video images to the display unit 72. Referring to FIG. 12, the camera 16 is comprised of a lens 56, a shutter 51, an image sensor 57, a processor or CPU 59, and a flex circuit 61. Images collected by the camera 16 are displayed on the screen 88 of the display unit 72. Although the camera 16 of the preferred embodiment produces video images, it can also generate still images which may also be displayed on the screen 88 of the display unit 72.

Referring to FIG. 5, in the preferred embodiment, the arm 14 is comprised of a heating unit 21. This heating unit 21 heats the light 20 and camera 16 area and prevents the light 20 and camera 16 from developing moisture which may obscure the images gathered by the camera 16. The heating unit 21 is comprised of a thermistor 23 which monitors the temperature of the heating unit 21 and shuts the unit 21 off when a predetermined temperature is reached. In the preferred embodiment, such temperature is approximately 120 degrees Fahrenheit. The arm 14 is further comprised of a flex circuit 61 (FIG. 5). This circuit 61 is capable of supplying power to the camera 16 light 20 and heating unit 21 as well as transmitting information (including images) between the camera 16 and display unit 72. The handle 16 and arm 14 are each further comprised of heater switch 53 and 55. When the laryngoscope 14 is in the folded position, the heater switch 53 and 55 is in the open position and no power to the heater unit 21 is transferred. In this folded position, connectors 52 are also open such that power is not transferred to the light 20, camera 16, and heating unit 21.

As shown in FIGS. 3 & 4, in alternative embodiments, a sheath 10 switch 25 is located on the arm 14. When the sheath 10 is in place and the arm 14 is in the working/engaged position as shown in FIGS. 2A and 2B, power is supplied to the heating unit 21. However, when the sheath 10 24 is not present, as shown in FIG. 3, or the arm 14 is in the folded/disengaged position depicted in FIG. 4, the heater switch 53, 55 is open, and no power is supplied to the heater unit 21. The sheath 10 switch 25 interrupts power to the handle portion 53 of heater switch 53, 55.

Figure 13:
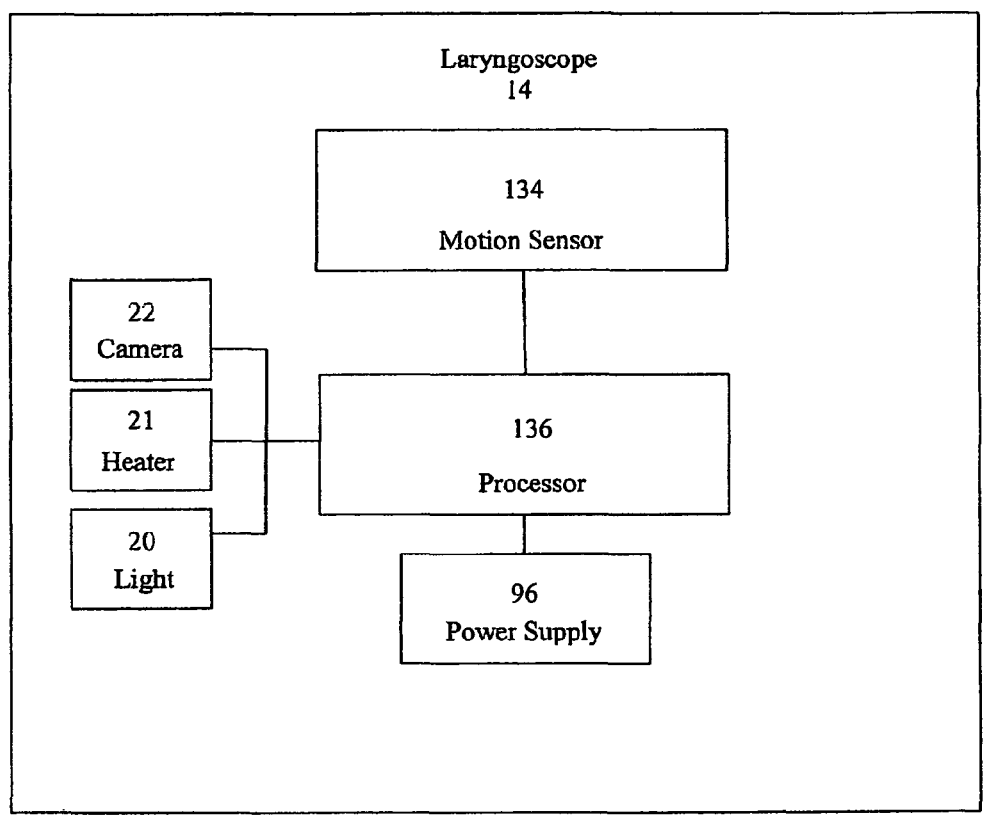
FIG. 13 is a block diagram depicting the laryngoscope motion sensor system.

The cord 96 further transmits power from a power source to the light 20 camera 16 and heating unit 21. Referring to FIG. 13, in one aspect of the present invention the laryngoscope 14 is comprised of a motion sensor 134 and processor 136 that allow the laryngoscope 14 to be motion activated such that the laryngoscope 14 is powered on upon a predetermined threshold of movement. In another aspect of the present invention, the laryngoscope 14 is capable of being motion activated such that the laryngoscope 14 is powered off when no movement is detected for a predetermined period of time.

In FIG. 3, there is shown the connection assembly between the handle 16 and arm 14. At the base of the handle 16 there is a pin 46 and ball spring receptacles 48. The arm 14 is comprised of ball springs 62. To couple the arm 14 to the handle 16, the pin 46 is inserted in arm 14 opening 47. The ball springs 62 slide into ball spring receptacles 48. This connection aligns arm 14 plate 64 with handle plate 50 within the walls 54 of handle plate 50 such that an electrical connection is made with connectors 52.

Figure 7:
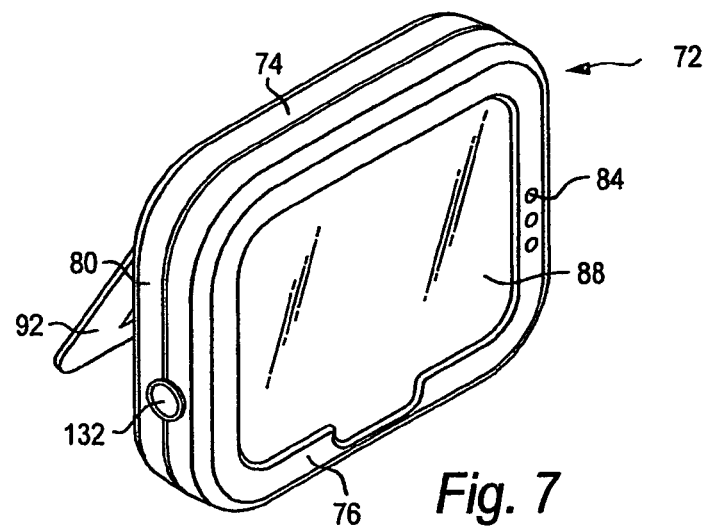
FIG. 7 is a top, front, and left side isometric view of the display unit with the stand in the open position.
Figure 8:
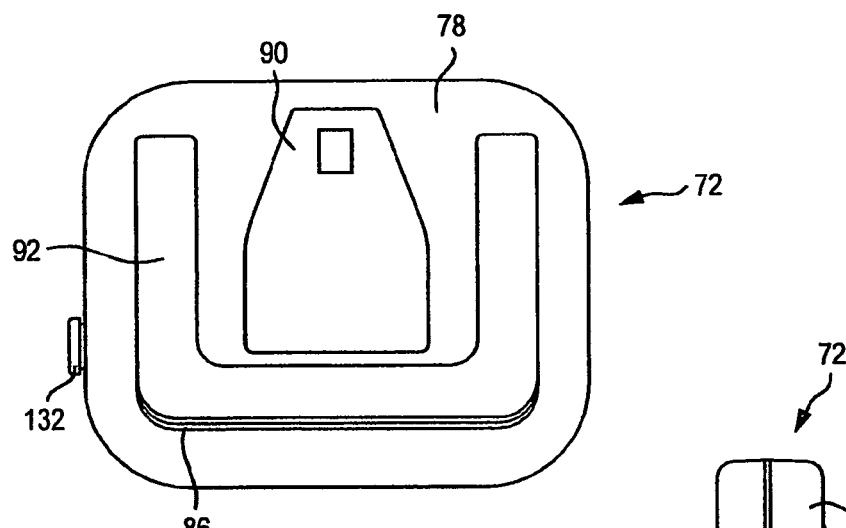
FIG. 8 is rear elevation view of the display unit with the stand in the open position.
Figure 9:
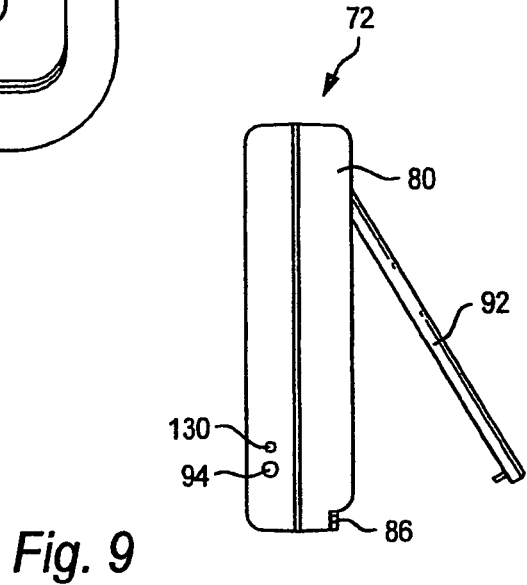
FIG. 9 is a right side isometric view of the display unit with the stand in the open position.

Referring to FIGS. 1 and 7-9, the display unit 72 is comprised of a thin container 74, a screen 88, a DC Jack 94, a battery management board and a battery. The container 74 is comprised of an IV pole attachment connector 90 such that it may be removably coupled to an IV pole attachment receiver 100 (FIG. 11) or, as shown in FIGS. 7 & 9, sit upright on a stand 92 when not attached to the IV pole attachment receiver 100. Referring to FIGS. 7-9, the container 74 of the preferred embodiment is generally rectangular and is comprised of a face 76, a back 78, and sides 80. The face 76 of the container 74 partially surrounds the screen 88 so that the screen 88 may be viewed. In the preferred embodiment, the stand 92 is pivotally coupled to the back 78 and is structured and arranged such that it extends generally rearward from the back 78 when in use and folds flat against the back 78 in a recess 86 when in the stored position. In the preferred embodiment, said recess 86 is contoured to the shape of the stand 92.

Figure 14:
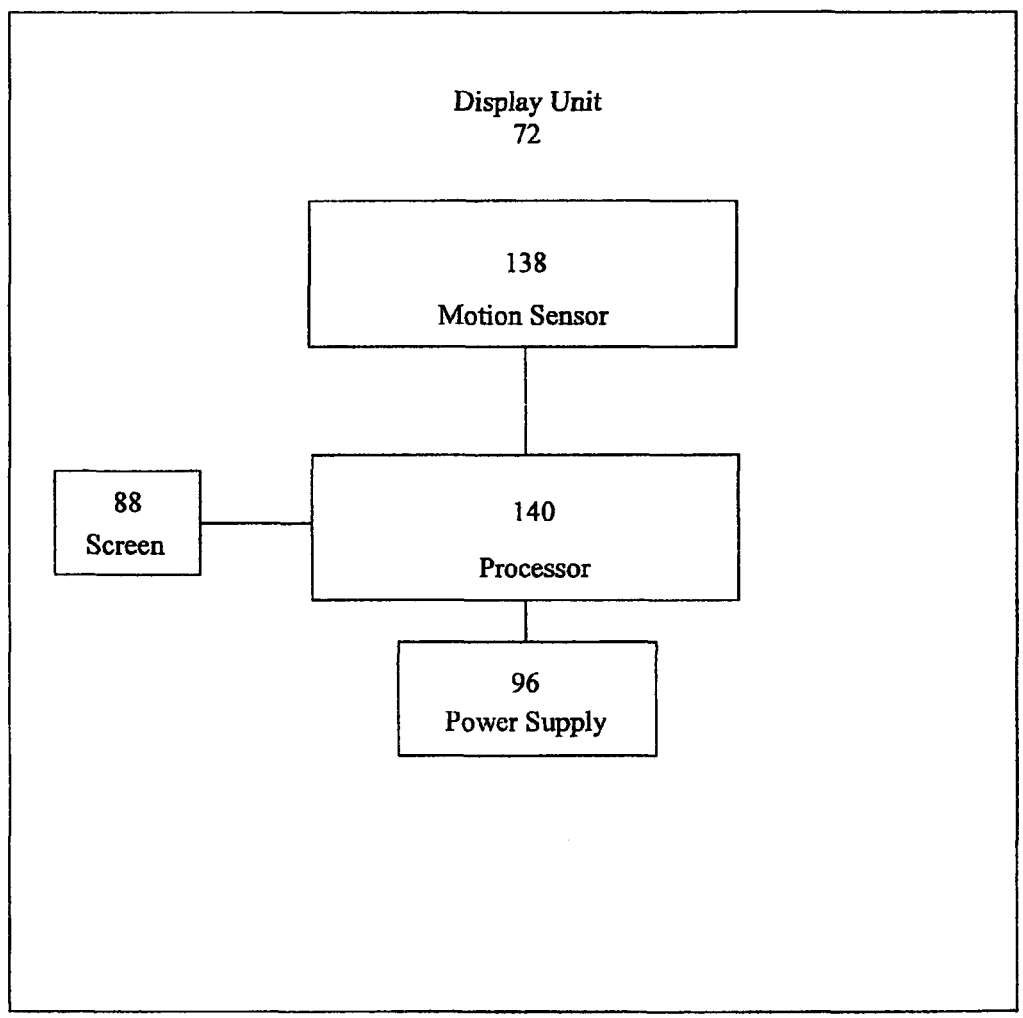
FIG. 14 is a block diagram depicting the display unit motion sensor system.

Referring to FIG. 14, in one aspect of the present invention the display unit 72 is comprised of a motion sensor 138 and processor 140 that allow the screen 88 to be motion activated such that the screen 88 is powered on upon a predetermined threshold movement. In another aspect of the present invention, the screen 88 is capable of being motion activated such that the screen 88 is powered off when no movement is detected for a predetermined period of time.

Referring again to FIGS. 7-9, in one aspect of the present invention, the face 76 has a battery status indicator 84. This indicator 84 is comprised of a plurality of LED 18 lights. In the preferred embodiment, two green lights showing indicate to the user that the battery is fully charged and the system 12 is operable. An amber light indicates the battery is depleted and will need to be charged soon. A red light indicates the battery lacks sufficient charge to operate the screen 88, camera 16, and light 20. In the preferred embodiment, the indicator 84 is positioned at the lower portion of the face 76 near the center and beneath the screen 88.

The back 78, on the inside, has pegs and receptacles which act as coupling devices. The central pegs of the back correspond with receptacles located on the reverse side of the screen 88. The perimeter receptacles correspond with pegs located on the inside side of the face 76.

The screen 88 and battery are mounted on the inside portion of the back 78 of the container 74. The battery of the preferred embodiment is a rechargeable lithium battery and is capable of illuminating the screen 88. The screen 88 of the preferred embodiment is a 3:5 inch (Diagonal) Liquid Crystal Display (LCD). The screen 88 displays the image captured by the camera 16. In one aspect of the present invention, the screen 88 also displays other information such as the battery charge level, time, date, and the like.

The display unit 72 is further comprised of a DC input jack 94 and charge indicator 130. This jack 94 accepts the barrel portion of a charging cable. This jack 94 connects with and is used to recharge the battery. The charge indicator 130 is an LED 18 light that, when lit, alerts the user that the battery is being charged. In one aspect of the present invention, the unit 72 may not be operated while the charge cable is inserted into the jack 94

Figure 15:
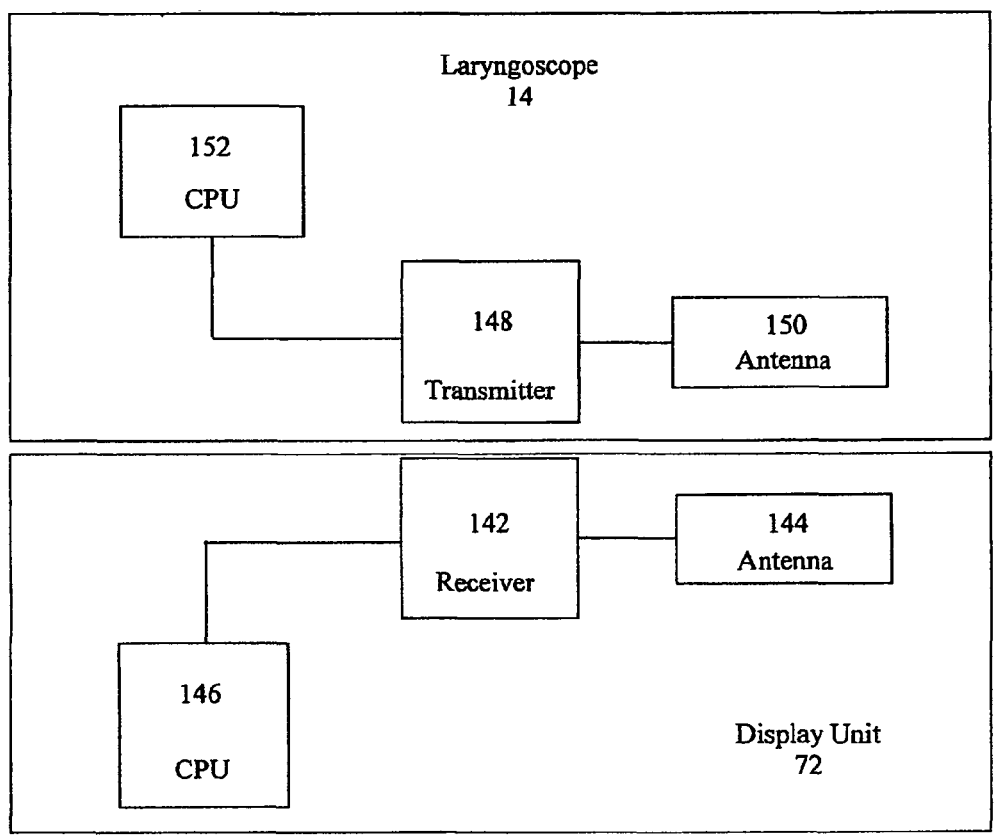
FIG. 15 is a block diagram depicting the laryngoscope and display unit wireless communication system.
Figure 16:
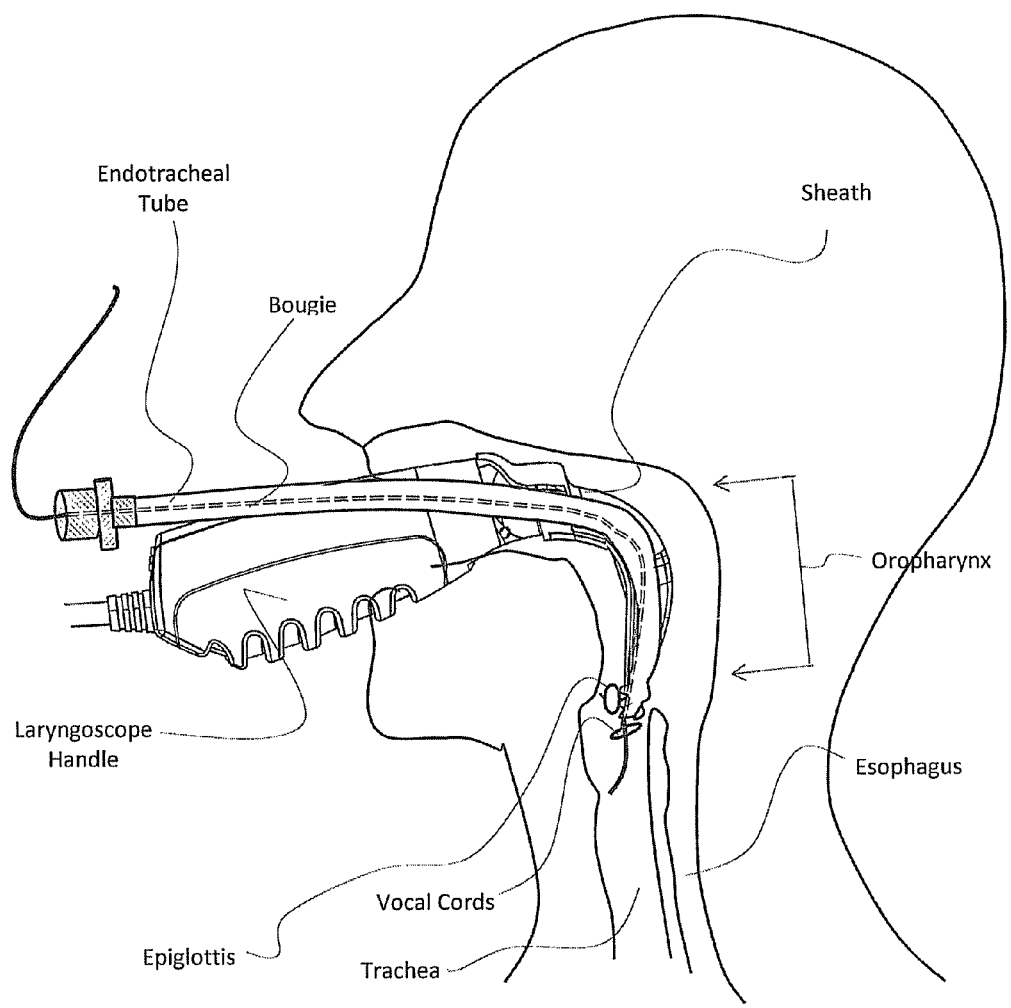
FIG. 16 is a side view of the laryngoscope and sheath, the bougie having been positioned within the trachea and an endotracheal tube threaded over the bougie, in accordance with a preferred embodiment of the method of the current invention (not to scale).

The cable 62 is capable of communicating images received from the camera 16 to the screen 88 through the communication jack 132. Referring to FIG. 15, in one aspect of the present invention, the laryngoscope 14 is capable of wirelessly communicating with the display unit 72. In this embodiment, the laryngoscope 14 is further comprised of a transmitter 148, a processor or CPU 152 and an antenna 150. The display unit 72 is further comprised of a receiver 142, a processor or CPU 146 and an antenna 144. Images captured by the camera 16 are processed by the CPU 152 and transmitted wirelessly to the display unit 72 receiver 142 such that the images are displayed on screen 88.

The communication cable 96 is also capable of transmitting power generated by the battery to the light 20 and camera 16. The battery management board is a conventional and commercially available circuit board and is capable of maintaining an appropriate charge level in the battery.

The IV pole 128 is conventional and commercially available. As may be seen in FIGS. 1 and 10-11, the IV pole attachment 98 is comprised of an attachment receiver 100, an IV pole clamp 108 with a C shaped opening, a tightening screw 110 with wing knob 112, and a laryngoscope receptacle 114. The attachment receiver 100 allows the user to quickly attach and separate the display unit 72 from IV pole attachment 98 and is comprised of a bracket 102, and a quick release button 104. The attachment connector 90 of the display unit 72 may be slideably attached to the attachment receiver 100. The user may detach the display unit 72 from the attachment receiver 100 by depressing the release button 104 which activates a lever 106 that disengages the display unit 72 from the attachment receiver 100. The IV pole attachment 98 may be secured to an IV pole 128 by inserting the pole 128 in the IV clamp's 108 C shape opening and tightening the tightening screw 110 with the wing knob 112.

Figure 10:
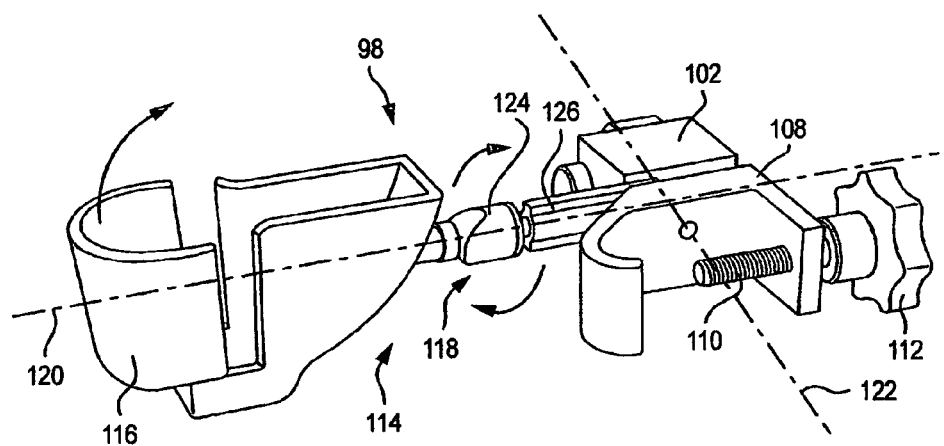
FIG. 10 is a rear isometric view of the IV pole attachment.
Figure 11:
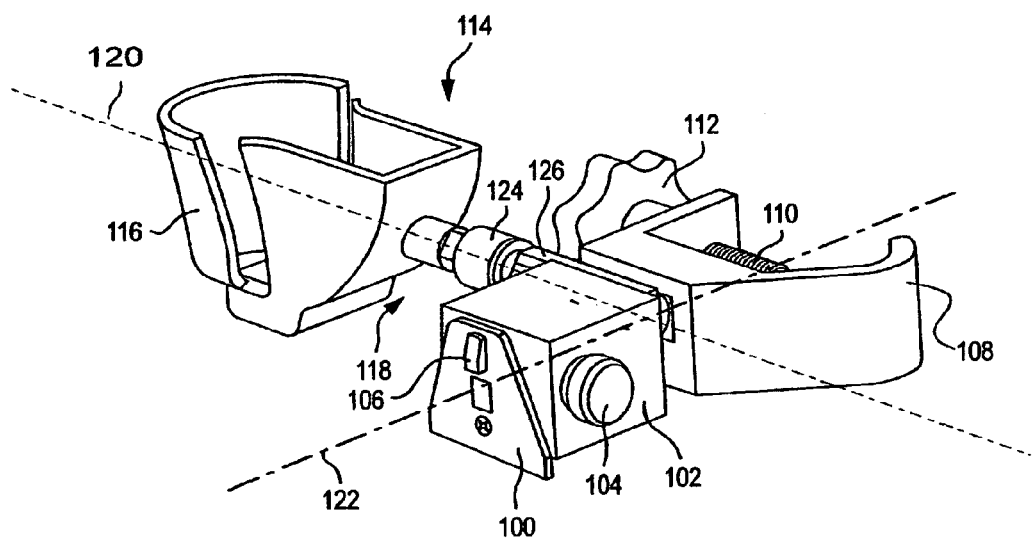
FIG. 11 is a front view of the IV pole attachment.

Referring to FIGS. 10-11, the laryngoscope receptacle 114 is comprised of a contoured holder 116 and an extension portion 118. The extension portion 118 is comprised of a first member 124 and a second member 126. In the preferred embodiment, the first member 124 is structured and arranged such that it can rotate 360 degrees around an imaginary axis 120 that extends from a longitudinal axis of the extension portion 118. The second member 126 is structured and arranged such that it can rotate up to 360 degrees around an axis 122 perpendicular to the axis 120 around which the first member 124 rotates. Therefore, as may be seen in FIGS. 10 and 11, the receptacle 114, without the need for the user detaching the IV pole attachment 98 from the IV pole 128, can be positioned on either side of an IV pole 128 and oriented such that the contoured holder 116 remains in an upright position and capable of receiving the laryngoscope 14.

The contoured holder 116 is shaped to accommodate the laryngoscope 14 in the folded position as shown in FIG. 4.

In the preferred embodiment the arm 14 is made from stainless steel. The handle 16 and container 74 are made from Acrylonitrile butadiene styrene (ABS). Although the handle 16 and container 74 of the preferred embodiment are formed from ABS, they need not be. For instance, the handle 16 and container 74 may be formed of any conventional material such as metal or plastic.

While there has been illustrated and described what is, at present, considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment-disclosed as the best mode contemplated for carrying out the invention, but that the invention will include all embodiments falling within the scope of this disclosure.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A method of endotracheal intubation comprising:
a first step comprising sliding an arm of a laryngoscope through a sheath comprising a c-shaped canal defining a side opening until a prong on the sheath engages a ridge on the arm to secure the sheath on the arm;
after the first step, performing a second step comprising manually grasping a handle of the laryngoscope, wherein the arm extends from the handle;
after the second step, performing a third step comprising placing the c-shaped canal into an oropharynx of a patient;
after the third step, performing a fourth step comprising threading a bougie into the c-shaped canal;
after the fourth step, performing a fifth step comprising threading an endotracheal tube over the bougie, advancing the endotracheal tube through the oropharynx, vocal cords, and trachea, and displacing the bougie out of the side opening.

2. The method of endotracheal intubation of claim 1 wherein the laryngoscope is a video laryngoscope.

3. The method of endotracheal intubation of claim 2 wherein said video laryngoscope is a adapted for use with a display unit.

4. The method of endotracheal intubation of claim 3 wherein said video laryngoscope communicates wirelessly with said display unit.

5. The method of endotracheal intubation of claim 1 wherein said arm is removably coupled to said handle.

6. The method of endotracheal intubation of claim 5 wherein said arm is curved.

7. The method of endotracheal intubation of claim 1 wherein said handle comprises an actuator, the actuator being biased towards a first position and moveable to a second position, and said actuator further comprising an actuator end, said actuator end extending into a coupling area when the actuator is in the second position.

8. The method of endotracheal intubation of claim 7 wherein said prong is scored and deformed when the actuator is moved to said second position.

9. The method of endotracheal intubation of claim 1 wherein said sheath is at least partially transparent.

10. The method of endotracheal intubation of claim 1 wherein said sheath comprises more than one prong.

11. The method of endotracheal intubation of claim 1 wherein said canal comprises a proximal end opening sharing a curved central longitudinal axis of the canal.

* * * * *